United States Patent
Campbell

[11] Patent Number: 5,928,193
[45] Date of Patent: Jul. 27, 1999

[54] BALLOON CATHETERIZATION

[75] Inventor: Andrew J. Campbell, Reading, Mass.

[73] Assignee: Boston Scientific Corporation, Natick, Mass.

[21] Appl. No.: 08/943,904

[22] Filed: Oct. 3, 1997

[51] Int. Cl.⁶ ................................................. A61M 29/00
[52] U.S. Cl. ........................... 604/96; 604/500; 604/103; 606/194
[58] Field of Search ............................. 604/96, 103, 101, 604/500; 606/191–194

[56] References Cited

U.S. PATENT DOCUMENTS

| | | |
|---|---|---|
| 3,960,143 | 6/1976 | Terada . |
| 4,018,231 | 4/1977 | Wallace . |
| 4,195,637 | 4/1980 | Grüntzig et al. . |
| 4,276,874 | 7/1981 | Wolvek et al. . |
| 4,292,974 | 10/1981 | Fogarty et al. . |
| 4,323,071 | 4/1982 | Simpson et al. . |
| 4,327,709 | 5/1982 | Hanson et al. . |
| 4,346,698 | 8/1982 | Hanson et al. . |
| 4,490,421 | 12/1984 | Levy . |
| 4,552,127 | 11/1985 | Schiff . |
| 4,846,174 | 7/1989 | Willard et al. . |
| 4,848,344 | 7/1989 | Sos et al. . |
| 4,968,300 | 11/1990 | Moutafis et al. . |
| 5,015,231 | 5/1991 | Keith et al. ......................... 604/103 X |
| 5,087,246 | 2/1992 | Smith .......................................... 604/96 |
| 5,350,361 | 9/1994 | Tsukashima et al. ..................... 604/96 |
| 5,395,333 | 3/1995 | Brill .......................................... 604/101 |
| 5,456,666 | 10/1995 | Campbell et al. . |

*Primary Examiner*—John D. Yasko
*Attorney, Agent, or Firm*—Fish & Richardson P.C.

[57] ABSTRACT

A medical balloon is collapsed to a small profile during deflation by preventing tension in the catheter or balloon which might otherwise direct the balloon into a larger diameter collapsed profile, making it difficult to remove the catheter from the body. Tension may be avoided by arranging at least one end of the balloon to slide with respect to the catheter body. The invention is particularly applicable to a relatively stiff, inelastic balloon that is preformed into a geometric cross-sectional shape with corners, such as a square balloon, for encouraging a particular collapsed configuration, e.g., three or more folded lobes.

33 Claims, 4 Drawing Sheets

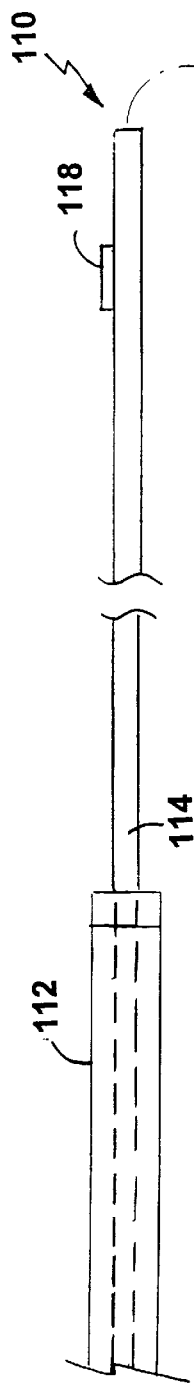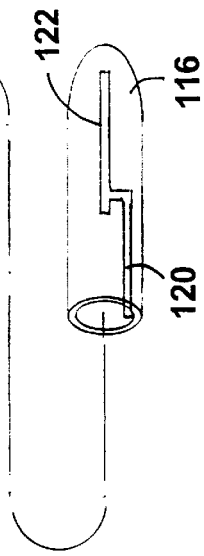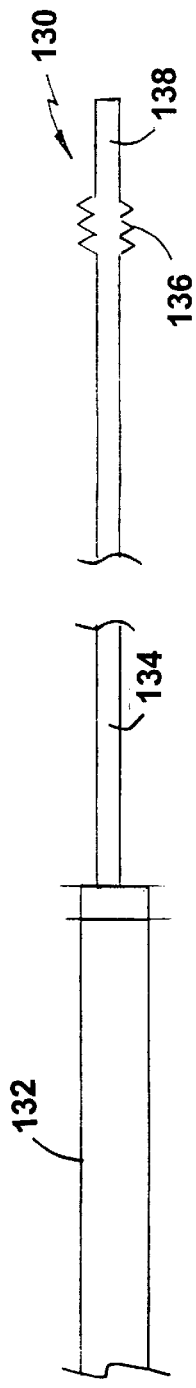
FIG. 9
FIG. 10
FIG. 11

BALLOON CATHETERIZATION

FIELD OF THE INVENTION

This invention relates to balloon catheterization.

BACKGROUND OF THE INVENTION

A balloon catheter is a device with an elongated shaft that carries an inflatable balloon. Typically, the shaft is delivered into a narrow body lumen with the balloon in a low profile deflated state. When the treatment site is reached, the balloon is inflated to its full diameter. After treatment is complete, the balloon is again deflated, hopefully to a small diameter profile, and the catheter is removed from the body. Inflation of the balloon may be effective to, for example, dilate the lumen, deliver a stent to the site, block the lumen, at least temporarily, stabilize the catheter, or deliver drugs to the lumen walls.

SUMMARY OF THE INVENTION

The invention relates to collapsing a balloon to a small profile during deflation by preventing tension in the catheter or balloon which might otherwise direct the balloon into a larger diameter collapsed profile, making it difficult to remove the catheter from the body. Tension in the catheter may be avoided by arranging at least one end of the balloon to slide with respect to the catheter. The invention is applicable to, for example, a relatively stiff, inelastic balloon that is preformed into a geometric cross-sectional shape with corners, such as a square balloon, for encouraging a particular collapsed configuration, e.g., three or more folded lobes.

In a first aspect, the invention features a balloon catheter with a flexible catheter body portion extending longitudinally, a spanning portion, and a tip region. The tip region is axially displacable with respect to the spanning portion between a retracted condition and an extended condition without biasing the spanning portion and tip region. The catheter also includes an inflatable balloon having a working portion and proximal and distal end portions. The proximal end portion is attached to the catheter body and the distal end portion is attached to the tip region. The working portion is preconditioned to form at least three lobes.

In another aspect, the invention features a balloon catheter with a flexible catheter body portion extending longitudinally from a region remaining outside the body to an end region positioned inside the body, a spanning portion extending through the flexible body portion from the region remaining outside the body and beyond the end region, and a tip region in sliding telescoping relationship with the spanning region between a retracted condition and an extended condition. An inflatable balloon is provided having a proximal and distal end portion. The distal end portion is attached to the tip region.

In another aspect, the invention features a method, including delivering a balloon catheter into the body, the balloon catheter including a catheter body extending longitudinally, a tip region, and an inflatable balloon. The balloon has proximal and distal end portions. The proximal end portion is attached to the flexible catheter body portion and the distal end portion is attached to the tip region. The method also includes inflating the balloon, during which the tip region is axially displaced with respect to the catheter body to a retracted condition without biasing the flexible catheter body and tip region.

Embodiments may include one or more of the following. The spanning portion is axially fixed relative to the catheter body portion. The tip region is an element concentrically arranged with respect to the spanning portion. The tip region includes a tubular element concentrically about the spanning portion. The tip is axially slidable relative to the spanning portion. The tip is arranged concentrically over a distal portion of the spanning portion. The spanning portion is a solid wire-member. The spanning portion is fixed to the flexible body portion. The spanning portion is a tubular member.

Embodiments may also include one or more of the following. The catheter body and tip region include lumens arranged to pass a guidewire through the balloon and beyond the tip member. The catheter spanning portion includes a lumen for passage of the guidewire. The tip region is articulated by a collapsible region. The tip region is in telescoping relationship.

Embodiments may also include one or more of the following. A strand element is attached between the catheter and the tip region. The strand element is in a slack condition, free of substantial bias when the tip region is in the retracted condition or extended condition. The tip member and catheter body have complementary mating structure. The tip member and catheter body have bayonet fitting structure. The catheter body has a spanning portion, spanning the interior of the balloon, the spanning portion being a continuous extension of the flexible catheter body portion. The catheter body, spanning portion, and tip-region include lumens for passage of the guidewire. The balloon is made of a substantially inelastic material. The balloon is made of PET. The balloon is inflated to open an obstructed lumen. The catheter is placed over a guidewire.

Implementations of the invention may have certain advantages. For example, reliable collapse of the balloon to small diameter makes it easier to withdraw the catheter from the body, particularly in cases where the catheter is drawn into another catheter, such as an introducer catheter or an endoscope.

Still further aspects, features, and advantages follow.

DESCRIPTION OF THE PREFERRED EMBODIMENTS

We first briefly describe the drawings.

Drawings

FIG. 9 is an exploded view of another catheter;

FIG. 10 is a side view of another catheter;

FIG. 11 is a cross-sectional side view of another catheter.

STRUCTURE AND OPERATION

Figure 1:
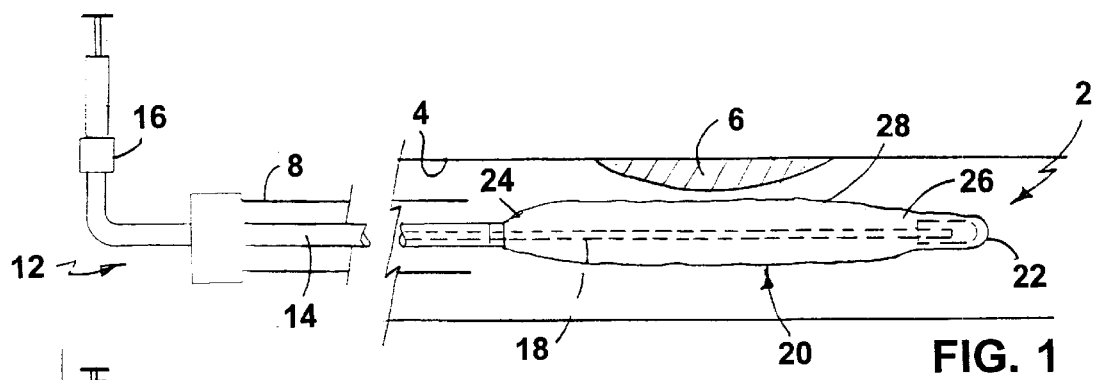
FIG. 1 is a cross-sectional side view of a balloon catheter with the balloon in the initial deflated condition as the catheter is delivered to a site where dilatation is to take place and FIG. 1a is an end-on cross-sectional view through the balloon and catheter.

Referring to FIGS. 1–6, a balloon catheter 2 may be delivered into a body lumen 4, such as the esophagus, for dilating a lesion 6. The catheter 2 is delivered through an endoscope 8 which extends from a coupling part 10, remaining outside the body, to an end positioned close to the lesion. The catheter 2 has a catheter body 12 including a flexible portion 14 which extends most of its length from a coupling 16. The catheter also has a spanning portion 18 which extends through the balloon 20. The catheter also includes a tip 22.

The balloon 20 includes proximal and distal end portions 24, 26 and a working portion 28. The proximal and distal end portions 24, 26 are attached to the catheter body and the tip 22. The tip 22 can slide axially with respect to the spanning portion 18 which prevents bias, i.e., tension or compression in the catheter or balloon as the balloon is inflated and deflated, particularly with a balloon that has been preformed with corners to preferentially collapse to a particular shape.

Figure 1A:

Referring particularly to FIGS. 1 and 1a, during delivery to the treatment site, the balloon is deflated and in an initial collapsed condition in which it is tightly wrapped about the catheter in a series of overlapping wings or lobes 30, preferably three or more. In this condition, the tip 22, while movable axially, does not slide substantially due to the resistance of the mass of the tightly wrapped balloon. The balloon in this small diameter form can be passed through the endoscope 8 and threaded to the dilatation site.

Figure 2:
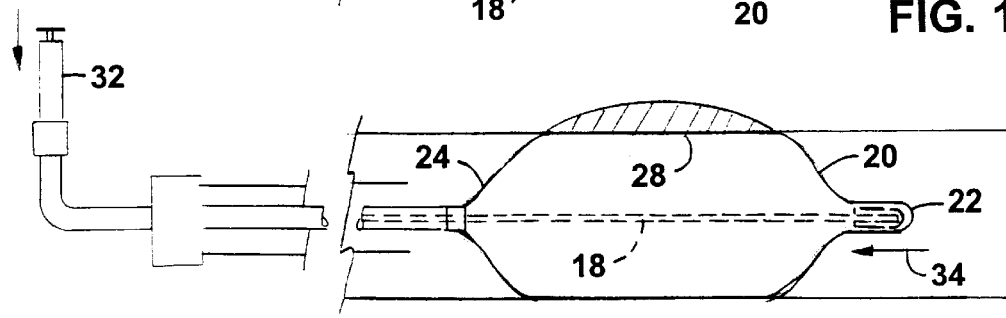
FIGS. 2 and 2a are views similar to FIGS. 1 and 1a with the balloon inflated and dilating the lumen.
Figure 2A:
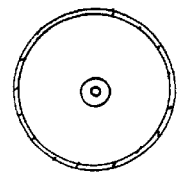

Referring particularly to FIGS. 2 and 2a, for dilating the site, the balloon is inflated so that the working portion 28 presses against the lumen wall, including the lesion 6 forcing the passageway open. During inflation, the lobes 30 of the folded balloon unfold and at full inflation the working portion of the balloon has a generally circular cross section as shown in FIG. 2a. Inflation may be achieved by an inflation/deflation controller 32, such as a syringe or other device which directs inflation fluid through the catheter body into the balloon. At full inflation, the ends 24, 26 of the balloon may be drawn together. With the end 26 attached to the tip 22, any compression biasing that might otherwise be placed on the catheter body, spanning member or tip 22 is avoided as the tip 22 slides (arrow 34) proximally over the spanning member 18.

Figure 3:
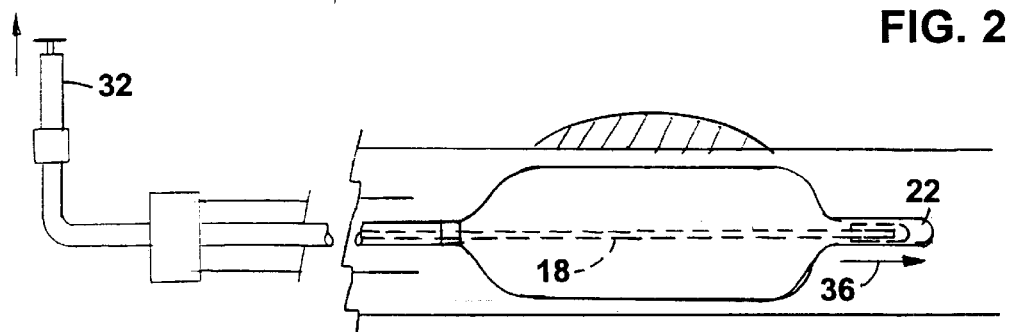
FIGS. 3 and 3a are views similar to FIGS. 1 and 1a with the balloon partially deflated after dilatation.
Figure 3A:
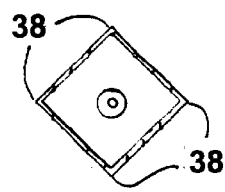

Referring to FIGS. 3 and 3a, after dilatation, the balloon is deflated by withdrawing fluid within the balloon and through the catheter body using controller 32. As the balloon deflates, the ends may be pushed apart. Any tension biasing in the catheter body, spanning portion or tip is avoided as the tip 22 slides (arrow 36) distally under the force of the collapsing mass of balloon material. In the intermediate stage of deflation, the balloon has a geometric shape with a series of corners 38 which assist further collapse of the balloon into a small profile. Avoiding tension in the catheter prevents forces from acting on the balloon which might disturb the collapse intended by the corners 38.

Figure 4:
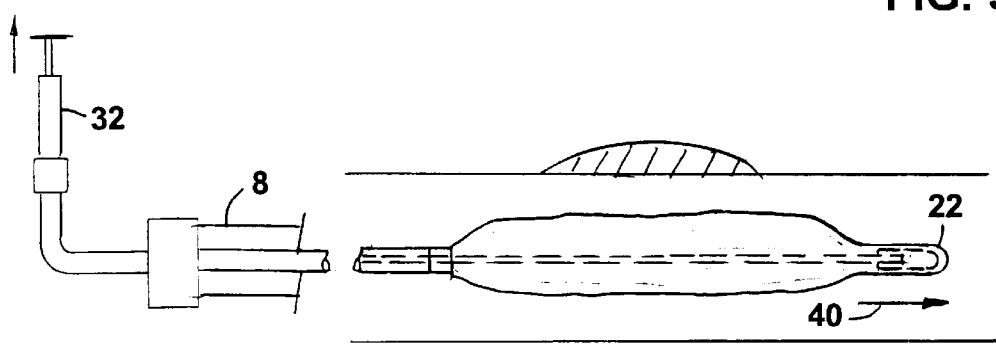
FIGS. 4 and 4a are views similar to FIGS. 1 and 1a with the balloon fully deflated after dilatation.
Figure 4A:
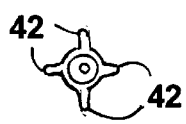

Referring to FIGS. 4 and 4a, further deflation of the balloon is achieved by creating a vacuum within the balloon again using controller 32. The tip 22 may continue axial movement as deflation continues (arrow 40). The profile of the balloon in the fully collapsed condition is a series of four lobes 42 in which the balloon has a sufficiently small diameter to be withdrawn through the endoscope 8.

Figure 5:
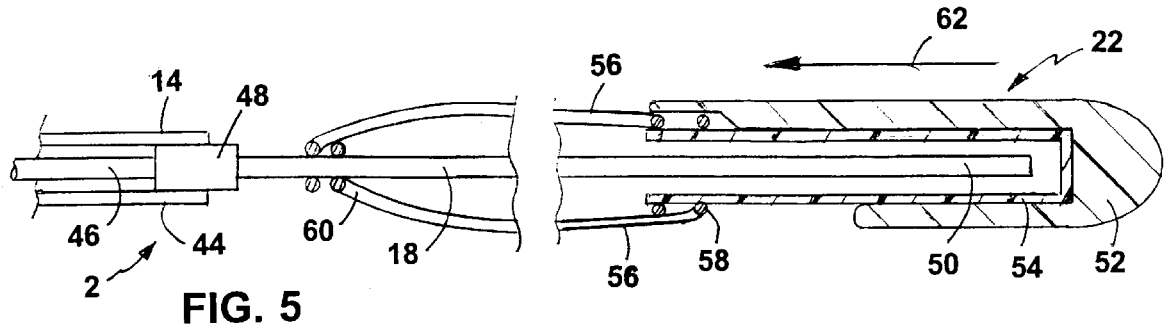
FIGS. 5 and 5a are cross-sectional side views of the catheter with the balloon removed and a slidable tip in retracted and extended conditions.
Figure 5A:
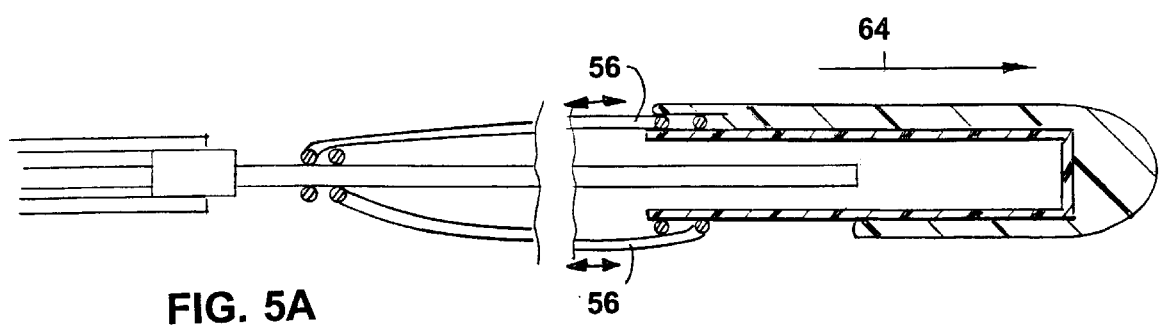
Figure 6:
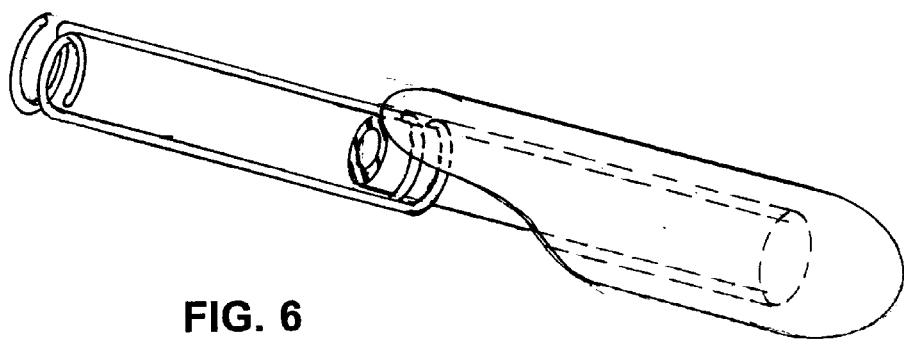
FIG. 6 is a perspective view of the tip assembly.

Referring to FIGS. 5–6, more detailed views of the catheter are provided. The flexible body portion 14 includes a flexible tubular sheath 44 and a core wire 46. The flexible sheath 44 terminates at an annular coupling 48. The core wire 46 is fixed to the coupling and extends beyond it, forming the spanning region 18 and terminating at an end region 50. The tip region 22 includes a polymeric tip member 52 which includes a lumen area with a hypotube 54 sized to slidably receive the end region 50 of the spanning portion 18. For safety, the tip region 22 is connected to the core wire by a series of wires 56. One end 58 of each is attached to the hypotube 54 and the other end 60 is attached to the spanning portion 18. As the tip region 22 slides proximally (arrow 62), the wires are in a slack condition. As the tip 22 slides distally (arrow 64), the wires 56 take up the slack but without creating tension.

In a particular embodiment, the catheter is designed for use in the esophagus. The catheter has an overall length of about 180 cm. The flexible body is formed of nylon and has outer diameter of about 0.078 inch, an inner diameter of about 0.061 inch, and length of about 170 cm. A metal tube, about 0.20 inch long with an inner diameter of about 0.052 inch, and a wall thickness of about 0.005 inch, is embedded in the distal end of the flexible body for attachment of the core wire. The core wire, made of stainless steel, has a diameter of about 0.023 inch and a length of about 180 cm, extending beyond the flexible shaft about 10 cm. The core wire is attached to the tube by welding. The core wire extends proximally through the catheter to the coupling where it is attached. The core wire enhances the pushability of the catheter, making it easier to urge it through the endoscope and body lumen without collapsing or buckling. The tip is made of PEBAX 3535 (Atochem, Philadelphia, Pa.) and has a outer diameter of about 0.075 inch, a wall thickness of about 0.022 inch, and a length of about 1 inch. The tip hypotube has an inner diameter of about 0.035 inch, a wall thickness of about 0.009 inch, and a length of about 0.75 inch. The hypotube is overmolded to the tip by injection molding. The flexible wires are made of stainless steel, have a diameter of about 0.005 inch and extend from the tip about 0.875 inch. They are attached to the tip tube and core wire by welding. Alternatively, the wires may be polymeric such as Kevlar or Vectron, in which case they are attached to the catheter by adhesive. The free sliding play of the tip on the core wire is about 0.750 inch. The balloon has a square shape and is made of PET. Balloon of this type are discussed in Campbell et al. U.S. Pat. No. 5,456,666, the entire contents of which is incorporated by reference. In embodiments, the balloon may be made of other materials such as compliant or semicompliant polymers. An example is a balloon made of PBT elastomer, such as Arnitel (polybutadieneterephthalate, available from PSM, the Netherlands).

Figure 7:
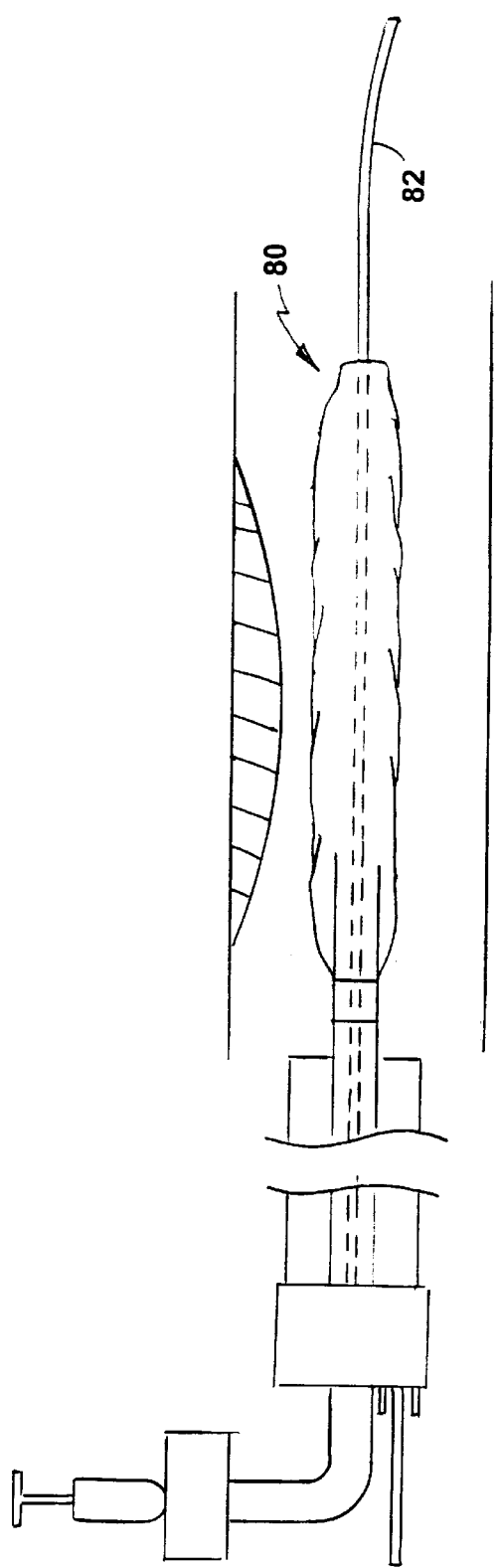
FIG. 7 is a side view of another balloon catheter during delivery to a treatment site.
Figure 8:
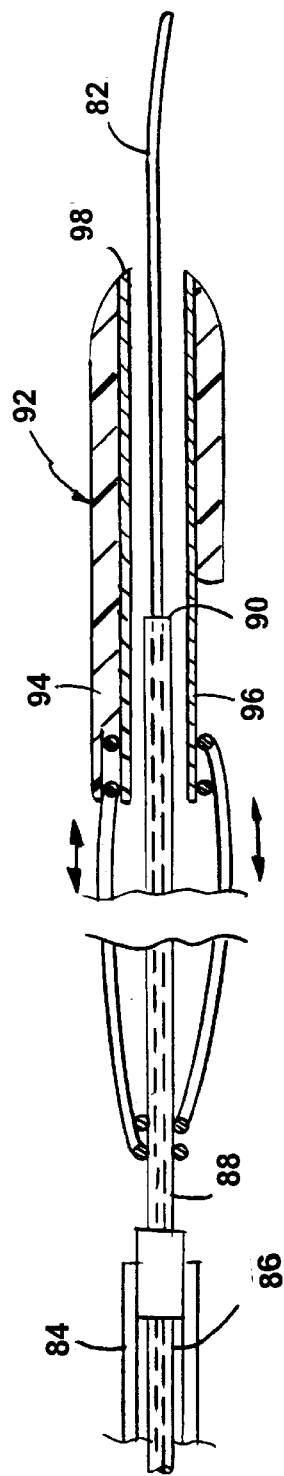
FIG. 8 is a cross-sectional side view of the catheter in FIG. 7.

Referring to FIGS. 7 and 8, in another embodiment, a catheter 80 is arranged for delivery into the body over an axially moveable guidewire 82. The guidewire 82 may be delivered into the lumen and then the catheter 80 slid over the guidewire 82. Referring particularly to FIG. 8, the catheter 80 includes a flexible polymeric catheter body 84 and a tube member 86 which extends through the body 84 and forms a spanning region 88. The tube member 86 terminates in an end opening 90. The catheter also includes a tip 92 with an outer polymeric body 94 and an inner tube member 86. The spanning tube 88 terminates within the inner tube 96 of the tip 92. The inner tube 96 includes an end opening 98. The catheter therefore provides a passageway from the catheter body, through the balloon and end of the tip region 92. The passage may extend proximally to the proximal end of the catheter outside the body and/or the guidewire may emerge from the catheter just proximal of the balloon for rapid exchange.

Referring to FIG. 9, in another embodiment, a catheter 110 includes a flexible polymeric tube 112, a core wire 114, and a slidable tip 116. The core wire 114 includes a nub 118 which can be engaged with a bayonet fitting 120 on the tip 116. The bayonet fitting includes a slot 122, permitting axial sliding motion of the tip 116 with respect to the catheter while preventing rotational motion about the catheter axis.

Referring to FIG. 10, a catheter 130 includes a flexible tubular body 132 and a core wire 134. The core wire extends to a bellows 136 which is attached to a tip region 138. The tip region 138 may be a segment of core wire material or it may be another material, such as a soft polymer. The bellows 136 permits axial motion of the tip 138 relative to the catheter body. The bellows may be manufactured of, for example, a highly flexible stainless steel or a superelastic material such as nitinol. In another embodiment, the bellows is replaced by a hinge arrangement. For example, a pair of radially opposed hinges may be provided with the arms of the hinges being attached to the core wire and the tip.

Referring to FIG. 11, a catheter 150 includes a continuous polymeric body 152 including a proximal region 154 and a spanning region 156. The catheter 150 also includes a tip member 158 which is slidably disposed over the distal portion of the spanning region 156. The catheter has a pair of lumens 160, 162. The lumen 160 is used for introducing inflation fluid to the balloon. The lumen 162 is for passing a guidewire. The lumen 162 terminates in a end opening 164 at the end of the spanning region 156. The slidable tip 158 includes an axially aligned end opening 166 for through passage of the guidewire from the distal end of the catheter.

Still further embodiments are within the following claims.

I claim:

1. A balloon catheter, comprising:
    a flexible catheter body portion extending longitudinally,
    a spanning portion, and a tip region,
    said tip region being axially displacable with respect to said spanning portion between a retracted condition and extended condition without biasing the spanning portion and tip region, and
    an inflatable balloon having a working portion and proximal and distal end portions, the distal end portion being attached to said tip region, and said working portion being preconditioned to form at least three lobes.

2. The catheter of claim 1 wherein said proximal end portion of said balloon is attached to the catheter body portion.

3. The catheter of claim 2 wherein the spanning portion is axially fixed relative to said catheter body portion.

4. The catheter of claim 1 wherein said tip region is an element concentrically arranged with respect to said spanning portion.

5. The catheter of claim 4 wherein said tip region includes a tubular element concentrically about said spanning portion.

6. The catheter of claim 5 wherein said tip is axially slidable relative to said spanning portion.

7. The catheter of claim 6 wherein said tip is arranged concentrically over a distal portion of said spanning portion.

8. The catheter of claim 7 wherein said spanning portion is a solid wire-member.

9. The catheter of claim 8 wherein said spanning portion is fixed to said flexible body portion.

10. The catheter of claim 1 wherein said spanning portion is a tubular member.

11. The catheter of claim 1 wherein said catheter body and tip region include lumens arranged to pass a guidewire through said balloon and beyond said tip member.

12. The catheter of claim 11 wherein said spanning portion includes a lumen for passage of said guidewire.

13. The catheter of claim 1 wherein the tip region is articulated by a collapsible region.

14. The catheter of claim 1 wherein said tip region is in telescoping relationship.

15. The catheter of claim 1 including a strand element attached between said catheter and said tip region.

16. The catheter of claim 15 wherein said strand element is in a slack condition, free of bias when said tip region is in the retracted condition or extended condition.

17. The catheter of claim 1 wherein said tip member and catheter body have complementary mating structure.

18. The catheter of claim 17 wherein said tip member and catheter body have bayonet fitting structure.

19. The catheter of claim 1 wherein said catheter body has a spanning portion, spanning the interior of said balloon, said spanning portion being a continuous extension of said flexible catheter body portion.

20. The catheter of claim 19 wherein said catheter body, spanning portion, and tip-region include lumens for passage of the guidewire.

21. The catheter of claim 1 wherein said balloon is made of a substantially inelastic material.

22. The catheter of claim 1 wherein said balloon is made of PET.

23. A balloon catheter, comprising:
    a flexible catheter body portion extending longitudinally from a region remaining outside the body to an end region positioned inside the body,
    a spanning portion extending through said flexible body portion from the region remaining outside the body beyond the end region, and
    a tip region in sliding telescoping relationship with said spanning region between a retracted condition and an extended condition,
    an inflatable balloon having a proximal and distal end portion, the distal end portion being attached to the tip region.

24. The catheter of claim 23 wherein said proximal end portion of said balloon is attached to the catheter body.

25. The catheter of claim 24 wherein the spanning portion is axially fixed relative to said catheter body portion.

26. The catheter of claim 25 wherein said catheter body, spanning portion, and tip region are unbiased when said tip region is in the extended or retracted condition.

27. The catheter of claims 23 or 26 wherein said balloon is substantially inelastic.

28. The catheter of claim 27 wherein said balloon is preconditioned to form at least three lobes.

29. A method, comprising:
    delivering a balloon catheter into the body, said balloon catheter including a catheter body extending longitudinally, a tip region, and an inflatable balloon, said balloon having proximal and distal end portions, the proximal end portion being attached to said flexible catheter body portion, and said distal end portion being attached to said tip region, inflating said balloon, during which said tip region is axially displaced with respect to said catheter body to a retracted condition without biasing said flexible catheter body and tip region.

30. The method of claim 29 comprising:

deflating said balloon and causing said tip region to be axially displaced with respect to said flexible catheter body portion to an extended condition in which the flexible catheter body portion and the tip region are unbiased.

31. The method of claim 30 wherein said balloon is preconditioned to form at least three lobes.

32. The method of any one of claim 29, 30, and 31 comprising inflating said balloon to open an obstructed lumen.

33. The method of claim 29 comprising delivering said catheter over a guidewire.

* * * * *